United States Patent [19]
Umehara et al.

[11] Patent Number: 4,643,990
[45] Date of Patent: * Feb. 17, 1987

[54] N-ACYL PEPTIDE, PROCESSES FOR THEIR PREPARATION AND PHARMACEUTICAL COMPOSITIONS THEREOF

[75] Inventors: Kazuyoshi Umehara, Ashiya; Keizo Yoshida, Suita; Hirokazu Tanaka, Takarazuka; Itsuo Uchida, Kyoto; Masanobu Kohsaka, Sakai; Hiroshi Imanaka, Mishima, all of Japan

[73] Assignee: Fujisawa Pharmaceuitcal Co., Ltd., Osaka, Japan

[*] Notice: The portion of the term of this patent subsequent to Mar. 18, 2001 has been disclaimed.

[21] Appl. No.: 452,827

[22] Filed: Dec. 23, 1982

[30] Foreign Application Priority Data

Jan. 5, 1982 [GB] United Kingdom ............... 8200212
Jun. 1, 1982 [GB] United Kingdom ............... 8215910

[51] Int. Cl.$^4$ .............. A61K 37/43; C07K 5/06; C07K 5/08; C07C 143/12; C07C 69/52; C07C 67/02; C07C 101/26; C07C 101/30

[52] U.S. Cl. ..................... 514/18; 530/331; 560/149; 560/222; 560/251; 560/252; 560/253; 560/169; 560/170; 260/998.2; 514/19

[58] Field of Search .............. 260/112.5 R, 998.2; 424/177; 560/253, 251, 149, 222, 252, 169, 170; 514/18, 19; 530/331

[56] References Cited

U.S. PATENT DOCUMENTS 3,538,070 11/1970 Geiger et al. ............ 260/112.5 R
3,893,992 7/1975 De Benneville ................ 530/323
4,205,069 5/1980 Beluzzi et al. ............ 260/112.5 R
4,221,675 9/1980 Schirmann et al. ............ 560/253
4,311,640 1/1982 Kuroda et al. ............ 260/112.5 R
4,436,726 3/1984 Umehara et al. ............ 260/112.5 R

FOREIGN PATENT DOCUMENTS 0011283 11/1979 European Pat. Off. ...... 260/112.5 R
866369 4/1961 United Kingdom .
2053232 6/1980 United Kingdom .

OTHER PUBLICATIONS

Derwent Publications & JP A 67 11 925, 1967.
Derwent Publications & JP A 71 08 685, 1971.
Derwent Publications & JP A 71 00 164, 1971.
Yasutaka Tahara, Masaru Kameda, Yuzo Yamada and Keiji Kondo, Agricultural and Biological Chemistry, 40(1), 243-244, 1976.

Primary Examiner—Delbert R. Phillips
Attorney, Agent, or Firm—Oblon, Fisher, Spivak, McClelland, & Maier

[57] ABSTRACT

N-acylpeptides are disclosed of the formula:

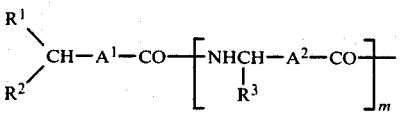

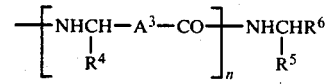

wherein $R^1$ is alkanoyloxy or alkenoyloxy; $R^2$ is alkyl or alkenyl; $R^3$ and $R^4$ are each lower alkyl, hydroxy(lower)alkyl, ar(lower)alkyl, esterified carboxy(lower)alkyl, carboxy(lower)alkyl, protected amino(lower)alkyl or amino(lower)alkyl; $R^5$ is hydrogen, hydroxy(lower)alkyl, protected amino(lower)alkyl, amino(lower)alkyl, carboxy(lower)alkyl or esterified carboxy(lower)alkyl; $R^6$ is carboxy, esterified carboxy or sulfo(lower)alkyl; $A^1$, $A^2$ and $A^3$ are each bond or lower alkylene; and m and n are each an integer of 0 or 1; or its pharmaceutically acceptable salt. These compounds have anti-complementary activity and fibrinolytic activity, and are useful as therapeutic agents for immune-complex diseases or autoimmune diseases such as nephritis, rheumatic diseases, systemic lupus erythematosus, etc. and thrombosis such as cerebral apoplexy, coronary insufficiency, pulmonary embolism, etc.

12 Claims, No Drawings

N-ACYL PEPTIDE, PROCESSES FOR THEIR PREPARATION AND PHARMACEUTICAL COMPOSITIONS THEREOF

BACKGROUND OF THE INVENTION

1. Field of the Invention

This invention relates to a new N-acylpeptide compound and pharmaceutically acceptable salts thereof.

More particularly, this invention relates to a new N-acylpeptide compound and pharmaceutically acceptable salts thereof, which have pharmacological activities, to processes for their preparation and to a pharmaceutical composition comprising the same.

2. Summary of the Invention

The N-acylpeptide compounds of this invention is novel and can be represented by the following formula:

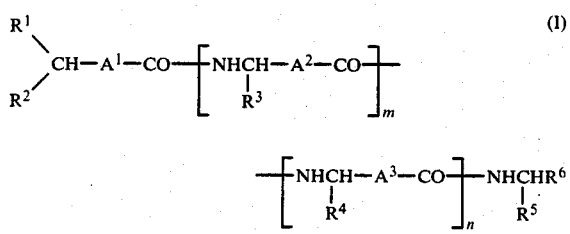

wherein
$R^1$ is hydrogen, alkanoyloxy or alkenoyloxy;
$R^2$ is alkyl or alkenyl;
$R^3$ and $R^4$ are each hydrogen, lower alkyl, hydroxy(lower)alkyl, ar(lower)alkyl, esterified carboxy(lower)alkyl, carboxy(lower)alkyl, protected amino(lower)alkyl or amino(lower)alkyl;
$R^5$ is hydrogen, hydroxy(lower)alkyl, protected amino(lower)alkyl, amino(lower)alkyl, carboxy(lower)alkyl or esterified carboxy(lower)alkyl;
$R^6$ is carboxy, esterified carboxy or sulfo(lower)alkyl;
$A^1$, $A^2$ and $A^3$ are each bond or lower alkylene; and
m and n are each an integer of 0 or 1.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

DESCRIPTION OF THE INVENTION

In the object compounds (I), the corresponding starting compounds (II) and (III) in Process 1, and (IIa) and (IIIa) in Process 2 mentioned below, it is to be understood that there may be one or more stereoisomeric pair(s) such as optical and geometrical isomers due to asymmetric carbon atom and double bond in those molecules and such isomers are also included within the scope of the present invention.

According to the present invention, the object compounds (I) and the pharmaceutically acceptable salts thereof can be prepared by the processes as illustrated by the following reaction schemes.

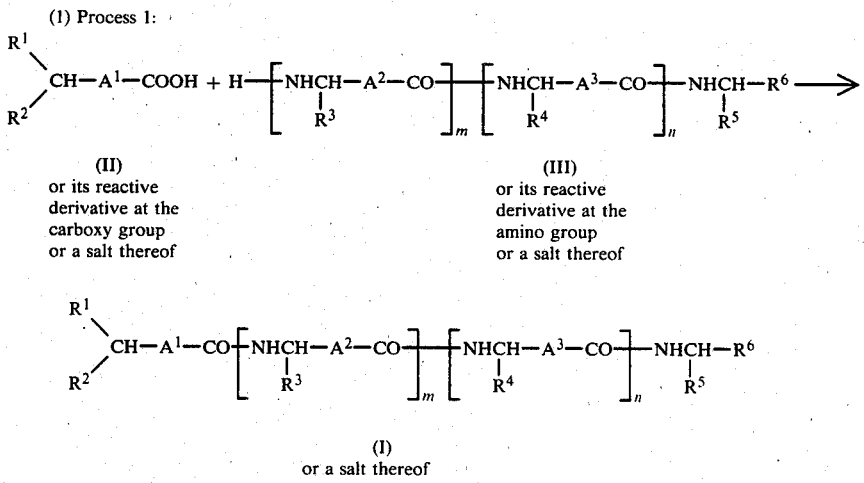

-continued (2) Process 2:

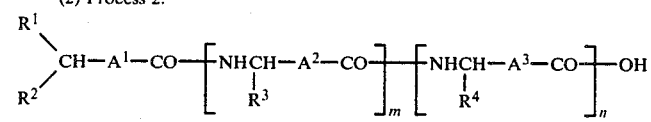

(IIa)
or its reactive
derivative at the carboxy group
or a salt thereof

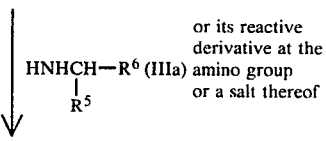

or its reactive
derivative at the
amino group
or a salt thereof

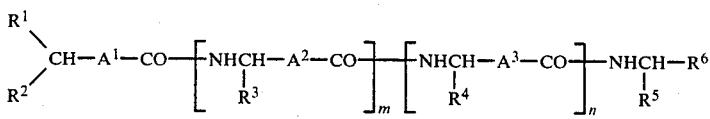

(I)
or a salt thereof (3) Process 3:

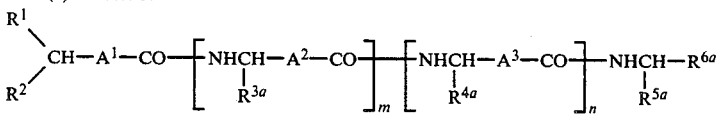

(Ia)
or its reactive derivative
at the carboxy group
or a salt thereof

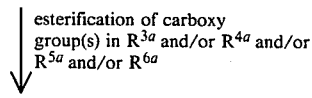

esterification of carboxy
group(s) in $R^{3a}$ and/or $R^{4a}$ and/or
$R^{5a}$ and/or $R^{6a}$

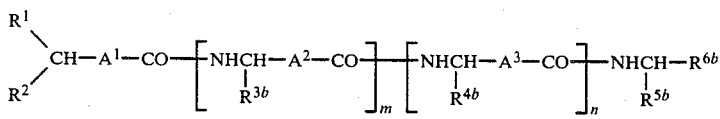

(Ib)
or a salt thereof (4) Process 4:

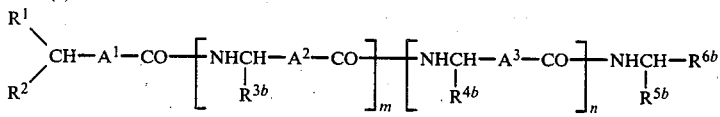

(Ib)
or a salt thereof

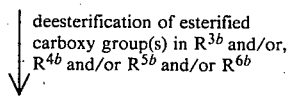

deesterification of esterified
carboxy group(s) in $R^{3b}$ and/or,
$R^{4b}$ and/or $R^{5b}$ and/or $R^{6b}$

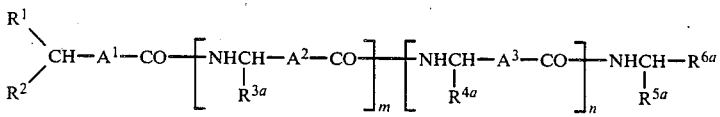

(Ia)
or a salt thereof (5) Process 5:

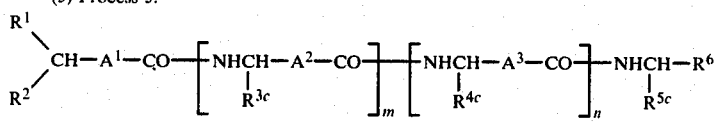

(Ic)
or a salt thereof

Elimination of the amino protective group(s)
in $R^{3c}$ and/or, $R^{4c}$ and/or $R^{5c}$

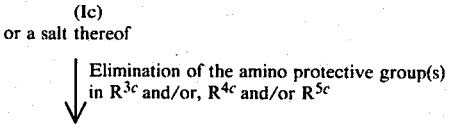

(Id)
or a salt thereof wherein
$R^1$, $R^2$, $R^3$, $R^4$, $R^5$, $R^6$, $A^1$, $A^2$, $A^3$, m and n are each as defined above,
$R^{3a}$, $R^{3b}$, $R^{3c}$, $R^{3d}$, $R^{4a}$, $R^{4b}$, $R^{4c}$ and $R^{4d}$ are each the same one as defined in $R^3$ and $R^4$,
and $R^{5a}$, $R^{5b}$, $R^{5c}$ and $R^{5d}$ are each the same one as defined in $R^5$,
and $R^{6a}$ and $R^{6b}$ are each the same one as defined in $R^6$, provided that
(i) at least one of $R^{3a}$, $R^{4a}$ and $R^{5a}$ is carboxy(lower)alkyl and/or $R^{6a}$ is carboxy,
(ii) at least one of $R^{3b}$, $R^{4b}$ and $R^{5b}$ is esterified carboxy(lower)alkyl and/or $R^{6b}$ is esterified carboxy,
(iii) at least one of $R^{3c}$, $R^{4c}$ and $R^{5c}$ is protected amino(lower)alkyl, and
(iv) at least one of $R^{3d}$, $R^{4d}$ and $R^{5d}$ is amino(lower)alkyl.

Some of the starting compounds (II) and (IIa) used in Process 1 and 2 are new and can be prepared, for example, from the known compound by the method in the following preparations or in a similar manner thereto or in a conventional manner.

Preparation 1:

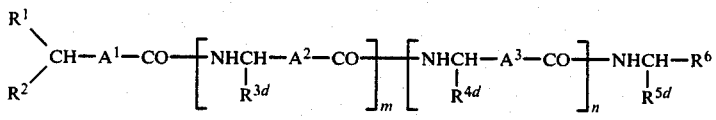

(IV)          (V)
(Reformatskii Reaction)

Preparation 2:

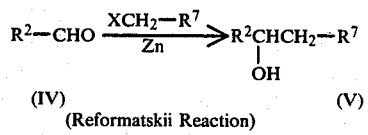

(V') or its reactive derivative at the carboxy group or a salt thereof    (II')

Preparation 3:

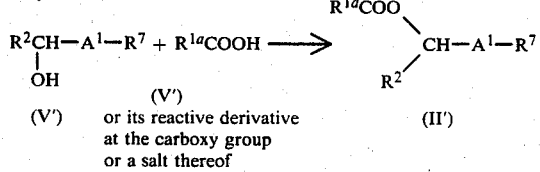

(II')          (II'')
or a salt thereof

Preparation 4:

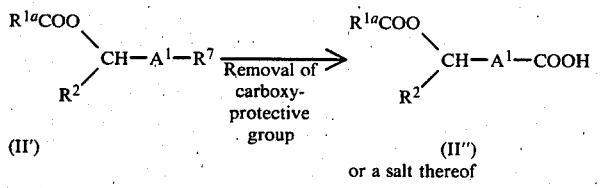

(II'')          (VII)
or its reactive derivative at the carboxy group or a salt thereof    or its reactive derivative at the amino group or a salt thereof

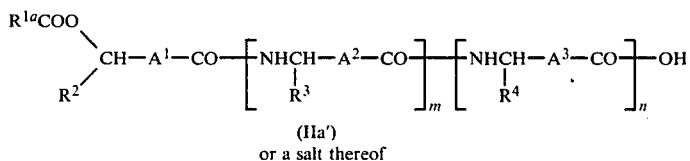

(IIa')
or a salt thereof wherein
$R^2$, $R^3$, $R^4$, $A^1$, $A^2$, $A^3$, m and n are each as defined above,
$R^{1a}$ is alkyl or alkenyl,
$R^7$ is protected carboxy and
X is halogen.

In the above and subsequent description of the present specification, suitable examples and illustration of the various definitions to be included within the scope thereof are explained in detail as follows.

The term "lower" in the present specification is intended to mean a group having 1 to 6 carbon atom(s), unless otherwise indicated.

Suitable "alkanoyloxy" may include straight or branched ones having 1 to 20 carbon atoms, such as formyloxy, acetoxy, propionyloxy, butyryloxy, isobutyryloxy, valeryloxy, isovaleryloxy, pivaloyloxy, hexanoyloxy, 4-methylbutanoyloxy, heptanoyloxy, 5-methylhexanoyloxy, octanoyloxy, 6-methylheptanoyloxy, nonanoyloxy, 7-methyloctanoyloxy, decanoyloxy, 8-methylnonanyloxy, undecanoyloxy, 9-methyldecanoyloxy, dodecanoyloxy, 10-methylundecanoyloxy, tridecanoyloxy, 11-methylundecanoyloxy, tetradecanoyloxy, 12-methyltridecanoyloxy, pentadecanoyloxy, 13-methyltetradecanoyloxy, hexadecanoyloxy, 14-methylpentadecanoyloxy, or the like in which the preferred one is C3–C20 alkanoyloxy.

Suitable "alkenoyloxy" may include straight and branched one having 3 to 20 carbon atoms, such as 13-methyl-4-tetradecenoyloxy, 9-octadecenoyloxy or the like.

Suitable "alkyl" may include straight and branched ones having 1 to 50 carbon atoms, such as methyl, ethyl, propyl, isopropyl, butyl, isobutyl, tert-butyl, pentyl, isopentyl, hexyl, isohexyl, heptyl, 5-methylhexyl, octyl, 6-methylheptyl, nonyl, 7-methyloctyl, decyl, 8-methylnonyl, undecyl, 9-methyldecyl, dodecyl, 10-methyldecyl, tridecyl, 11-methyldodecyl, tetradecyl, 12-methyltridecyl, pentadecyl, 13-methyltetradecyl, hexadecyl, 14-methylpentadecyl, heptadecyl, 15-methylhexadecyl, octadecyl, 16-methylheptadecyl, nonadecyl, 17-methyloctadecyl, eicosyl, 18-methylnonadecyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetracontyl, pentacontyl, or the like, in which the preferred one is C3–C30 alkyl.

Suitable "alkenyl" may include straight and branched one having 3 to 20 carbon atoms, such as 12-methyl-3-tridecenyl, 8-heptadecenyl or the like.

Suitable "lower alkyl" and "lower alkyl moiety" in the terms "hydroxy(lower)alkyl", "ar(lower)alkyl", "esterified carboxy(lower)alkyl", "carboxy(lower)alkyl", "protected amino(lower)alkyl", "amino(lower)alkyl" and "sulfo(lower)alkyl" may include straight and branched ones having 1 to 6 carbon atoms such as methyl, ethyl, propyl, isopropyl, butyl,isobutyl, tert-butyl, pentyl, isopentyl, hexyl, isohexyl and the like.

Suitable "aryl moiety" in the term "ar(lower)alkyl", may include phenyl, tolyl, xylyl and the like.

Suitable "ester moiety" in the terms "esterified carboxy" and "esterified carboxy(lower)alkyl" may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), amino- and carboxy-substituted-lower alkyl ester (e.g. 2-amino-2-carboxyethyl ester, 3-amino-3-carboxypropyl ester, etc.), protected amino- and protected carboxy-substituted-lower alkyl ester such as lower alkoxycarbonylamino- and mono(or di to tri)phenyl(lower)alkoxycarbonyl-substituted-lower alkyl ester (e.g. 2-tert-butoxycarbonylamino-2-benzhydryloxycarbonylethyl ester, 3-tert-butoxycarbonylamino-3-benzhydryloxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propoionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like.

Suitable "amino-protective group" in the term "protected amino(lower)alkyl" may include a conventional amino-protective group, for example, acyl as mentioned below, ar(lower)alkyl such as mono-(or di or tri)-phenyl(lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), and the like.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), amidino, and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono(or di or tri)halo(lower)alkanoyl (e.g. chloracetyl, bromoacetyl, dichloroacetyl, trifluoroacetyl, etc.), mono(or di or tri)halo(lower)alkoxycarbonyl (e.g. chloromethoxycarbonyl, dichloromethoxycarbonyl, 2,2,2-tri-chloroethoxycarbonyl, etc.), nitro(or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

Suitable "lower alkylene" may include one having 1 to 6 carbon atom(s) such as methylene, ethylene, trimethylene, tetramethylene, pentamethylene, hexamethylene and the like.

Suitable "protected carboxy" may include an esterified carboxy group which is conventionally used in peptide chemistry.

Suitable "halogen" may include chlorine, bromine or iodine.

The processes 1 to 5 for the preparation of the object compound (I) of the present invention are explained in details in the following.

(1) Process 1:

The compound (I) or a salt thereof can be prepared by reacting the compound (II) or its reactive derivative at the carboxy group or a salt thereof with the compound (III) or its reactive derivative at the amino group or a salt thereof.

Suitable salt of the starting compound (II) may include the same salt with a base as illustrated for the compound (I), and suitable salt of the starting compound (III) may include the same one as illustrated for the compound (I).

Suitable reactive derivative at the carboxy group of the compound (II) may include, for example, an acid halide, an acid anhydride, an activated ester, an acid azide, and the like, and preferably an ester with a N-hydroxy compound such as N-hydroxysuccinimide, N-hydroxyphthalimide, 1-hydroxybenzotriazole, 1-hydroxy-6-chlorobenzotriazole, etc.), and the like.

Suitable reactive derivative at the amino group of the compound (III) may include a conventional one, for example, a silyl derivative formed by the reaction of the compound (III) with a silyl compound such as bis(trimethylsilyl)acetamide or trimethylsilylacetamide, and the like.

The suitable reactive derivatives of the compound (II) or (III) can optionally be selected from the above according to the kinds of the compounds (II) or (III) to be used practically.

This reaction can be carried out in the presence of an organic or inorganic base such as alkali metal (e.g. lithium, sodium, potassium etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like.

In case that the compound (II) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], N-ethoxycarbonyl-2-ethoxy-1,2-dihydroquinoline; a ketenimine compound (e.g. pentamethyleneketene-N-cyclohexylimine, diphenylketene-N-cyclohexylimine, etc.), N,N-carbonylbis(2-methylimidazole; an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water.

The reaction temperature is not critical and the reaction is usually carried out under cooling to warming.

(2) Process 2:

The compound (I) or a salt thereof can also be prepared by reacting the compound (IIa) or its reactive derivative at the carboxy group or a salt thereof with the compound (IIIa) or its reactive derivative at the amino group or a salt thereof.

Suitable salt of the starting compound (IIa) may include the same salt with a base as illustrated for the compound (I), and suitable salt of the starting compound (IIIa) may include the same one as illustrated for the compound (I).

Suitable reactive derivative at the carboxy group of the compound (IIa) and suitable reactive derivative at the amino group of the compound (IIIa) may be the same ones as exemplified in the Process 1.

This reaction can be carried out according to the same manner to that of Process 1.

(3) Process 3:

The compound (Ib) or a salt thereof can be prepared by subjecting the compound (Ia) or its reactive derivative at the carboxy group or a salt thereof, to esterification.

Suitable salt of the compound (Ia) may be referred to that of the compound (I) illustrated above, and suitable reactive derivative at the carboxy group of the compound (Ia) may be referred to that of the compound (I) illustrated in the Process 1.

The esterification can be conducted by reacting a compound (Ia) or its reactive derivative at the carboxy group or a salt thereof with a conventional esterifying agent such as an alcohol or its reactive equivalent (e.g. halide, sulfonate, sulfate, diazo compound, etc.) and the like.

The reaction can also be carried out in the presence of a base, and suitable examples thereof are the same as those given in the explanation of Process 1, and can preferably be carried out in the presence of metal iodide (e.g. sodium iodide, etc.).

This reaction is usually carried out in a conventional solvent which does not adversely influence the reaction such as N,N-dimethylformamide, tetrahydrofuran, dioxane, methanol, ethanol, etc., or a mixture thereof.

The reaction temperature is not critical, and the reaction is usually carried out under cooling to at somewhat elevated temperature.

In case that the alcohol per se is used as the esterifying agent, the reaction can also be carried out in the presence of a condensing agent as illustrated in Process 1.

(4) Process 4:

The compound (Ia) or a salt thereof can be prepared by subjecting the compound (Ib) or a salt thereof to deesterification of the esterified carboxy group(s) of the compound (Ib).

This reaction is carried out by a conventional method such as hydrolysis, reduction, and the reaction conditions (e.g. temperature, solvent, etc.) are substantially the same as those illustrated below for the elimination of the amino protective group(s) of the compound (Ic) in Process 5, and therefore are to be referred to said explanation.

(5) Process 5:

The compound (Id) or a salt thereof can be prepared by subjecting the compound (Ic) or a salt thereof to elimination of the amino-protective group(s).

Suitable method for this elimination reaction may include conventional one such as hydrolysis, reduction, combined methods comprising iminohalogenation and the like.

(i) For hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), a mixture thereof, an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for this hydrolysis can be selected according to the kinds of the protective group to be removed, for example, this hydrolysis can preferably be applied to the amino-protective group such as substituted or unsubstituted lower alkoxycarbonyl, substituted or unsubstituted lower alkanoyl.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are liquid.

The reaction temperature of this hydrolysis is not critical, and the reaction is usually carried out under cooling to at somewhat elevated temperature.

(ii) For reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromous chloride, chromous acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed, for example, the chemical reduction can preferably be applied to the amino-protective group for such as halo(lower)alkoxycarbonyl and the like, and catalytic reduction can preferably be applied to that such as substituted or unsubstituted ar(lower)alkoxycarbonyl, and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

The Preparation 1 to 4 for the preparation of the starting compounds of the present invention are explained in details in the following.

Preparation 1

This reaction can be carried out in accordance with so called Reformatskii reaction. Namely, this reaction can be carried out by reacting the compound (IV) with the compound of the formula: $XCH_2-R^7$ in the presence of metal such as zinc, magnesium, lithium, aluminum, cadmium or the like.

This reaction may be carried out preferably in the presence of iodine.

This reaction may be usually carried out in a solvent such as benzene, ether, tetrahydrofuran, etc. or the mixture thereof at ambient temperature or under heating.

Preparation 2

The compound (II') is prepared by acylating a hydroxy group of the compound (V') with the carboxylic acid (VI) or its reactive derivative at the carboxy group.

The reactive derivative may include an acid halide, an acid anhydride, an activated ester and the like.

The reaction is conducted in a conventional solvent such as pyridine, etc. under cooling to heating.

Preparation 3

The compound (II'') or a salt thereof can be prepared by subjecting a compound (II') to removal reaction of carboxy-protective group in $R^7$. This process can be conducted by hydrolysing or reducing the compound (II').

The method of hydrolysis includes a conventional one using an organic or inorganic acid such as formic acid, trifluoroacetic acid, benzenesulfonic acid, hydrochloric acid, or the like. The reaction is conducted in the presence or absence of a solvent at the ambient temperature or under warming. The method of reduction includes a conventional one which is illustrated in the description for Process 5.

Preparation 4

The compound (IIa') or a salt thereof can be prepared by reacting the compound(II'') or its reactive derivative at the carboxy group or a salt thereof with the compound (VII) or its reactive derivative at the amino group or a salt thereof.

Suitable salt of the starting compound (II'') may include the same salt with a base as illustrated for the compound (I), and suitable salt of the starting compound (VII) may include the same one as illustrated for the compound (I).

Suitable reactive derivative at the carboxy group of the compound (II'') and suitable reactive derivative at the amino group of the compound (VII) may be the same ones as exemplified in the Process 1.

This reaction can be carried out according to the same manner as that of Process 1.

The compound (I) of this invention has anti-complementary activity and fibrinolytic activity, and is useful as a therapeutic agent for immune-complex diseases or autoimmune diseases such as nephritis, rheumatic diseases, systemic lupus erythematosus, etc. and thrombosis such as cerebral apoplexy, coronary insufficiency, pulmonary embolism, etc.

Test results on the pharmacological effects of the compound (I) of this invention are shown below.

(1) Anticomplementary activity:

The anticomplementary activity of the test compound was measured according to the test method as described in Experimental Immunochemistry, edited by E. A. Kabat and M. M. Mayer, 2nd ed., Springfield, Ill: C. C. Thomas (1961) pages 133–240.

A mixture of 1 ml of a 5-fold diluted solution of a Veronal buffer solution containing $1.5 \times 10^{-4}M$ $Ca^{2+}$ and $5 \times 10^{-4}M$ $Mg^{2+}$ and isotonic gelatin, 1.5 ml of complement serum (guinea pig complement) diluted 400 times with a physiological saline solution and 0.05 ml of a solution of a test compound (in this case, a test compound was dissolved in a physiological saline solution) was incubated at 37° C. for 30 minutes. To the said mixture there was added 0.4 ml of sensitized erythrocytes suspension containing $5 \times 10^8$ cells/ml and said mixture was incubated at 37° C. further for 60 minutes. After the incubation, the mixture was centrifuged in 3,000 rpm at 4° C. for 10 minutes.

The absorbance ($OD_{541}$) of the supernatant separated was measured at 541 nm, and the extent that the test compound inhibited the hemolysis of the sensitized erythrocytes was determined. The 50% hemolysis inhibitory activity value (μg/ml) ($IC_{50}$) measured by the above method is shown in Table 1.

The results are expressed in Table 1 as the concentration of each drugs inhibiting the hemolysis activity by 50% ($IC_{50}$).

TABLE 1

| Test compound (Example No.) | Anticomplementary activity ($IC_{50}$) (μg/ml) |
| --- | --- |
| 3 | 1.89 |
| 6 | 0.49 |
| 7 | 3.4 |
| 8 (2) | 0.67 |
| 10 | 1.00 |
| 14 | 0.52 |
| 18 | 0.34 |
| 19 (2) | 5.28 |
| 36 | 9.5 |
| 37 | 0.13 |
| 39 | 1.67 |
| 42 | 0.06 |
| 43 | 30 |

(2) Fibrinolytic activity:

The enhancement of the fibrinolytic activity of the test compounds was measured according to the modified diluted whole blood clot lysis time method described in G. R. Fearnley, G. V. Balmforth, E. Fearnley: Clin. Sci. 16, 645–650 (1957) I. S. Chohan et al: Thrombos. Diathes. Haemorrh. 33, 226 (1975) and I. M. Nilsson et al: Handbook of Experimental Pharmacology 46, 110.

(i) Test method:

Fresh rabbit blood was diluted 20 times with 1/15M phosphate buffer (pH 7.4). A mixture of 400 μl of the diluted blood solution and 50 μl of a test compound (300 μg/ml) was incubated at 37° C. for 30 minutes. To the mixture were added 50 μl of urokinase solution (100 IU/ml) and 50 μl of bovine thrombin (100 N.I.H. u/ml). The clot produced in tubes was incubated at 37° C. for various periods of time. At the end of each incubation interval (15 minutes interval), 2.5 ml of distilled water was added to lyse erythrocytes released from clotted blood and absorbance ($OD_{541}$) of the supernatant separated by centrifugation (3,000 rpm for 10 minutes) from the reaction mixture was measured. The fibrinolytic activity of the test compound was determined by the time in minutes needed for the complete lysis of the blood clot.

(ii) Results:

The test results are shown in Table 3.

In the absence of a test compound, it took more than 2 hours to lyse blood clot in the above condition. However, blood clot was lysed in the presence of test compounds after 15 minutes (symbol: ++) and 45 minutes (symbol: +) incubation, respectively. Samples which were incapable of lysing blood clot within 1 hour incubation were expressed as symbol (−).

TABLE 2

| Test compound (Example No.) | Fibrinolytic activity |
|---|---|
| 3 | ++ |
| 6 | + |
| 7 | + |
| 8 (2) | ++ |
| 10 | + |
| 21 | + |
| 37 | + |
| 42 | ++ |

The compound (I) of this invention in admixture with pharmaceutically acceptable carriers can be administered to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropyl-cellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the object compounds is to be varied depending on various factors such as kind of diseases, weight and/or age of a patient, and further the kind of administration route.

The following Preparations and Examples are given for the purpose of illustrating this invention.

Preparation A-1

(1) A suspended solution of activated zinc (118 mg), a small crystal of iodine, and tetrahydrofuran (3 ml) was stirred under refluxing. To the mixture was added a solution of tert-butyl bromoacetate (312 mg) and 13-methyltetradecanal (226 mg) in tetrahydrofuran (3 ml), and the reactants were stirred under refluxing for 1 hour. Anhydrous conditions were maintained throughout this experiment. The cooled solution was poured into 0.1N hydrochloric acid (5.6 ml) and the resultant solution was adjusted to pH 2.0 with 2N hydrochloric acid. The excess of zinc was filtered off and the crude products were extracted with ethyl acetate. The ethyl acetate layer was washed with aqueous sodium hydrogen carbonate solution and brine, and then dried over magnesium sulfate. The ethyl acetate was evaporated off under reduced pressure to give the crude ester, which was purified by column chromatography on silica gel (Merck) and eluted with a mixture of cyclohexane and ethyl acetate (19:1). The fractions containing the object compound were combined and concentrated under reduced pressure. The residue was dried by high vacuum pump to afford an oil of tert-butyl 3-hydroxy-15-methylhexadecanoate (180 mg).

IR (film): 3450, 2920, 2850, 1715 cm$^{-1}$.

NMR (CDCl$_3$, δ): 4.0 (1H, m), 3.0 (1H, d, J=4 Hz), 2.3 to 2.43 (2H, m), 1.5 (9H, s), 1.05 to 2.0 (23H, m), 0.87 (6H, d, J=6 Hz).

(2) Thionyl chloride (1 ml) was added to a solution of 13-methyltetradecanoic acid (250 mg) in dry benzene (3 ml), and the resulting mixture was refluxed for 1 hour. After excess thionyl chloride and benzene were distilled off, the residue was taken up in benzene and the solution was evaporated off under reduced pressure. The residual acid chloride which was dried by high vacuum pump was dissolved in pyridine (3 ml) and to the solution was added a solution of tert-butyl 3-hydroxy-15-methylhexadecanoate (69 mg) in pyridine (1 ml). The resulting mixture was heated at 80° C. overnight. The cooled reaction mixture was poured into ice water, and the mixture was stirred for 30 minutes, acidified with 1N hydrochloric acid, extracted with ethyl acetate, washed with brine and dried over magnesium sulfate. After evaporation of the solvent, the residue was subjected to column chromatography on silica gel (Merck) and eluted with a mixture of hexane and ethyl acetate (97:3). The fractions containing the object compound were combined and concentrated under reduced pressure. The residue was dried up by high vacuum pump to afford an oil of tert-butyl 15-methyl-3-(13-methyltetradecanoyloxy)hexadecanoate (85 mg).

IR (film): 2900, 2820, 1725 cm$^{-1}$.

NMR (CDCl$_3$, δ): 5.2 (1H, m), 2.47 (2H, d, J=6 Hz), 2.2 (2H, t, J=6 Hz), 1.45 (9H, s), 1.1 to 1.9 (44H, m), 0.88 (12H, d, J=6 Hz).

(3) To tert-butyl 15-methyl-3-(13-methyltetradecanoyloxy)hexadecanoate (500 mg) was added trifluoroacetic acid (5 ml) and the mixture was stirred at ambient temperature for 2 hours. Excess trifluoroacetic acid was distilled off under reduced pressure. Dry benzene was added to the residue and the solvent was evaporated off. This operation was repeated three times. The residue was dried up by using high vacuum pump to afford an oil of 15-methyl-3-(13-methyltetradecanoyloxy)hexadecanoic acid (400 mg).

IR (film): 2950, 2850, 1725, 1710 cm$^{-1}$.

NMR (CDCl$_3$, δ): 6.5 (1H, broad s), 5.24 (1H, m), 2.6 (2H, d, J=6 Hz), 2.3 (2H, t, J=7 Hz), 2.0 to 1.0 (44H, m), 0.86 (12H, d, J=6 Hz).

Preparation A-2

(1) To a solution of 2,2-dimethyl-1,3-dioxane-4,6-dione (Meldrum's acid, 72 g) in dichloromethane (1 l) was added pyridine (81 ml). Then, palmitoyl chloride (150.7 g) was added thereto at 0° C. The mixture was stirred at 0° C. for 1 hour and for additional 2 hours at ambient temperature. The reaction mixture was diluted with chloroform (1 l), poured into ice water (1 l), acidified with dilute hydrochloric acid solution, and washed with water (500 ml×3). After drying over magnesium sulfate, the solvent was evaporated under reduced pressure to give 2,2-dimethyl-5-(1-hydroxyhexadecylidene)-1,3-dioxane-4,6-dione (200 g) as an oil.

IR (CHCl$_3$): 2940, 2860, 1820, 1735, 1660, 1570 cm$^{-1}$.

NMR (CDCl$_3$, δ): 3.1 (2H, t, J=8 Hz), 1.72 (6H, s), 1.6 to 1.2 (26H, m), 1.86 (3H, t, J=6 Hz).

(2) 2,2-Dimethyl-5-(1-hydroxyhexadecylidene)-1,3-dioxane-4,6-dione (200 g) and tert-butyl alcohol (170 g) were refluxed in benzene (1 l) for 4 hours. Evaporation of the solvent gave crude tert-butyl 3-oxooctadecanoate (185 g) as an oil.

IR (CHCl$_3$): 2940, 2860, 1730, 1705 cm$^{-1}$.

NMR (CDCl$_3$, δ): 3.35 (2H, s), 2.5 (2H, t, J=7 Hz), 1.5 (9H, s), 1.5 to 1.1 (26H, m), 0.85 (3H, t, J=7 Hz).

(3) To a solution of tert-butyl 3-oxooctadecanoate (130 g) in methanol (700 ml) was added sodium borohydride (15 g) at 0° C. in a portionwise. The mixture was stirred for 1 hour at 0° C. To the reaction mixture was added ice water and from this whole the object compound was extracted with ethyl acetate. The ethyl acetate solution was washed with water, dried over magnesium sulfate and then evaporated to give a residue which was dried up by using high vacuum pump to afford crude tert-butyl 3-hydroxyoctadecanoate (126.6 g) as an oil.

IR (Nujol): 3430, 2910, 2840, 1720 cm$^{-1}$.

NMR (CDCl$_3$, δ): 4.0 (1H, m), 3.3 (1H, d, J=4 Hz), 2.32 to 2.44 (2H, m), 1.48 (9H, s), 1.22 to 1.73 (28H, m), 0.9 (3H, t, J=6 Hz).

(4) To tert-butyl 3-hydroxyoctadecanoate (120 g) in pyridine (500 ml) was added palmitoyl chloride (120 g) at 0° C. The mixture was stirred at 0° C. for 5 hours and then allowed to stand over-night at room temperature. Pyridine was removed under reduced pressure and the residue was poured into water. The resulting mixture was stirred at ambient temperature for 2 hours, acidified with 1N HCl, extracted with ethyl acetate, and washed with water. Evaporation of the solvent gave a residue which was purified by silica gel column chromatography (30% CH$_2$Cl$_2$—CCl$_4$) to afford tert-butyl 3-hexadecanoyloxyoctadecanoate (160 g) as an oil.

IR (film): 2910, 2850, 1730 cm$^{-1}$.

NMR (CDCl$_3$, δ): 5.25 (1H, m), 2.48 (2H, d, J=7 Hz), 2.2 (2H, t, J=6 Hz), 1.47 (9H, s), 1.1 to 1.95 (54H, m), 0.09 (6H, t, J=6 Hz).

(5) To tert-butyl 3-hexadecanoyloxyoctadecanoate (156 g) was added trifluoroacetic acid (200 ml) at 0° C. After the temperature of the mixture was reached to ambient temperature, the resulting solution was allowed to stand at the same temperature for 3 hours. Excess trifluoroacetic acid was distilled off under reduced pressure. The residue was taken up in benzene and the solvent was evaporated off. This operation was repeated twice to remove trifluoroacetic acid completely. The residue was recrystallized from petroleum ether in refrigerator to afford crystals of 3-hexadecanoyloxyoctadecanoic acid (125 g).

IR (CHCl$_3$): 2920, 2850, 1720 cm$^{-1}$.

NMR (CDCl$_3$, δ): 5.2 (1H, m), 2.58 (2H, d, J=6 Hz), 2.3 (2H, t, J=7 Hz), 1.9 to 1.0 (54H, m), 0.88 (6H, t, J=6 Hz).

Preparation A-3

α-Hydroxypalmitic acid (3.2 g) was dissolved in pyridine (15 ml), and palmitoyl chloride (3.3 g) was added thereto at 0° C. The resulting mixture was allowed to stand overnight at room temperature. The reaction mixture was poured into water and the aqueous solution was stirred at room temperature for 1 hour, followed by acidification with 1N hydrochloric acid, and extraction with ethyl acetate. The extract was washed with water, dried over magnesium sulfate and concentrated to give a residue which was recrystallized from petroleum ether to afford crystals of 2-hexadecanoyloxyhexadecanoic acid (5.4 g). M.p. 55°–56° C.

IR (CHCl$_3$): 2940, 2860, 1720 cm$^{-1}$.

NMR (CDCl$_3$, δ): 5.1 (1H, m), 2.4 (2H, m), 2.1 to 1.1 (52H, m), 0.95 (6H, t, J=6 Hz).

Preparation A-4

(1) Starting from 9-octadecenoyl chloride (15 g) and 2,2-dimethyl-1,3-dioxane-4,6-dione (8 g), 5-(1-hydroxy-9-octadecenylidene)-2,2-dimethyl-1,3-dioxane-4,6-dione (18 g) was obtained as an oil according to similar manner to that of Preparation A-2 (1).

(2) Starting from 5-(1-hydroxy-9-octadecenylidene)-2,2-dimethyl-1,3-dioxane-4,6-dione (18 g) and tert-butyl alcohol (200 ml), tert-butyl 3-oxo-11-eicosenoate (13 g) was obtained as an oil according to a similar manner to that of Preparation A-2 (2).

(3) Starting from tert-butyl 3-oxo-11-eicosenoate (13 g), tert-butyl 3-hydroxy-11-eicosenoate (11.76 g) was obtained as a colorless oil according to a similar manner to that of Preparation A-2 (3).

IR (CHCl$_3$): 3530, 2940, 2860, 1710 cm$^{-1}$.

NMR (CDCl$_3$, δ): 5.4 (2H, m), 3.9 (1H, m), 3.03 (1H, d, J=4 Hz), 2.4 (2H, d, J=6 Hz), 2.0 (4H, m), 1.5 (9H, s), 1.7 to 1.1 (24H, m), 0.85 (3H, t, J=6 Hz).

(4) Starting from tert-butyl 3-hydroxy-11-eicosenoate (11 g) and 9-octadecenoyl chloride (15 g), tert-butyl 3-(9-octadecenoyloxy)-11-eicosenoate (14 g) was obtained as an oil according to a similar manner to that of Preparation A-2 (4).

IR (CHCl$_3$): 2950, 2880, 1725 cm$^{-1}$.

NMR (CDCl$_3$, δ): 5.4 to 5.1 (5H, m), 2.5 (2H, d, J=7 Hz), 2.4 to 1.8 (10H, m), 1.8 to 1.1 (46H, m), 1.45 (9H, s), 0.85 (6H, t, J=7 Hz).

(5) Starting from tert-butyl 3-(9-octadecenoyloxy)-11-eicosenoate (14 g), 3-(9-octadecenoyloxy)-11-eicosenoic acid (10.2 g) was obtained as powder according to a similar manner to that of Preparation A-2 (5).

IR (CHCl$_3$): 2950, 2880, 1725 cm$^{-1}$.

NMR (CDCl$_3$, δ): 9.7 (1H, s), 5.5 to 5.0 (5H, m), 2.6 (2H, d, J=7 Hz), 2.9 to 1.8 (10H, m), 1.9 to 1.0 (46H, m), 0.85 (6H, t, J=6 Hz).

Preparation B-1

3-Hexadecanoyloxyoctadecanoic acid (10.8 g) prepared by the method described in Preparation A-2 (5) and N-hydroxysuccinimide (2.3 g) was dissolved in dioxane (60 ml). N,N'-Dicyclohexylcarbodiimide (4.2 g) was added thereto under ice cooling. The mixture was stirred at ambient temperature over-night. The crystallized N,N'-dicyclohexylurea was filtered off and the filtrate was concentrated to give a residue. The residue was dissolved in N,N-dimethylformamide (70 ml). To this solution was added a solution of L-valine (5.85 g) and triethylamine (6.95 ml) in water (50 ml) at 0° C. The resulting mixture was stirred at ambient temperature overnight. The reaction mixture was acidified with 1N hydrochloric acid, extracted with ethyl acetate, washed with water and dried over magnesium sulfate. Ethyl acetate was distilled off to give a residue which was crystallized from petroleum ether to give crystals of N-(3-hexadecanoyloxyoctadecanoyl)-L-valine (8 g).

IR (CHCl$_3$): 2930, 2850, 1720, 1660 cm$^{-1}$.

NMR (CDCl$_3$, δ): 5.2 (1H, m), 4.5 (1H, m), 2.5 (2H, d, J=6 Hz), 2.35 (2H, t, J=6 Hz), 1.8 to 1.1 (61H, m), 0.95 (6H, t, J=7 Hz).

Preparation B-2

Starting from 2-hexadecanoyloxyhexadecanoic acid (2.55 g) prepared by the method described in Preparation A-3 and L-valine (2.34 g), N-(2-hexadecanoyloxyhexadecanoyl)-L-valine (2.5 g) was obtained as crystals according to a similar manner to that of Preparation B-1.

IR (CHCl$_3$): 2940, 2860, 1728, 1680 cm$^{-1}$.

NMR (CDCl$_3$—CD$_3$OD, δ): 5.15 (1H, m), 4.5 (1H, m), 2.4 (2H, m), 2.0 to 1.1 (53H, m), 0.9 (12H, m).

Preparation B-3

(1) To a solution of 3-(9-octadecenoyloxy)-11-eicosenoic acid (10 g) in dioxane (100 ml) were added N-hydroxysuccinimide (2 g) and N,N'-dicyclohexylcarbodiimide (3.5 g). The mixture was stirred at ambient temperature overnight and then filtered to remove N,N'-dicyclohexylurea. The filtrate was condensed and dried up by using a high vacuum pump to give N-hydroxysuccinimide ester of 3-(9-octadecenoyloxy)-11-eicosenoic acid (9.3 g).

(2) To a solution of N-hydroxysuccinimide ester of 3-(9-octadecenoyloxy)-11-eicosenoic acid (3 g) in N,N-dimethylformamide (30 ml) was added a solution of L-valine (4.42 g) and a 1N sodium hydroxide solution (37 ml) at 0° C. The resulting mixture was stirred at ambient temperature overnight. The reaction mixture was acidified with 1N hydrochloric acid solution, extracted with ethyl acetate, washed with water and dried over magnesium sulfate. Ethyl acetate was distilled off to give powder of N-[3-(9-octadecenoyloxy)-11-eicosenoyl]-L-valine (2.7 g).

Preparation B-4

Starting from 3-hexadecanoyloxyoctadecanoic acid (150 mg) prepared by the method described in Preparation A-2 (5) and N-β-alanyl-L-threonine (110 mg), N-[N-(3-hexadecanoyloxyoctadecanoyl)-β-alanyl]-L-threonine (95 mg) was obtained as powder according to similar manner to that of Preparation B-1.

IR (CHCl$_3$): 3350, 2925, 2850, 1725, 1640 cm$^{-1}$.

NMR (CDCl$_3$:CD$_3$OD=1:1, δ): 5.2 (1H, m), 4.5 to 4.1 (2H, m), 3.42 (2H, m), 2.6 to 2.2 (6H, m), 1.8 to 1.0 (57H, m), 0.9 (6H, t, J=6 Hz).

Preparation B-5

Starting from 3-hexadecanoyloxyoctadecanoic acid (10.8 g) prepared by the method described in Preparation A-2 (5) and β-alanine (5.36 g), N-[3-hexadecanoyloxyoctadecanoyl]-β-alanine (9.33 g) was obtained as crystals according to a similar manner to that of Preparation B-1.

IR (CHCl$_3$): 2940, 2850, 1720, 1660 cm$^{-1}$.

NMR (CDCl$_3$—CD$_3$OD, δ): 5.2 (1H, m), 3.5 (2H, m), 2.7 to 2.3 (6H, m), 1.9 to 1.2 (54H, m), 0.95 (6H, t, J=7 Hz).

Preparation B-6

Starting from 3-hexadecanoyloxyoctadecanoic acid (5.38 g) prepared by the method described in Preparation A-2 (5) and 5-aminopentanoic acid (5 g), N-(3-hexadecanoyloxyoctadecanoyl)-5-aminopentanoic acid (5.7 g) was obtained as crystals according to a similar manner to that of Preparation B-1. M.p. 66°–67°.

IR (CHCl$_3$): 2940, 2860, 1720, 1660 cm$^{-1}$.

NMR (CDCl$_3$—CD$_3$OD, δ): 5.2 (1H, m), 3.25 (2H, m), 2.4 (6H, m), 1.9 to 1.1 (58H, m), 0.95 (6H, t, J=6 Hz).

Preparation B-7

Starting from 3-hexadecanoyloxyoctadecanoic acid (1 g) prepared by the method described in Preparation A-2 (5) and L-phenylalanine (1 g), N-(3-hexadecanoyloxyoctadecanoyl)-L-phenylalaline (500 mg) was obtained as powder according to a similar manner to that of Preparation B-1.

NMR (CDCl$_3$—CD$_3$OD, δ): 5.2 (1H, m), 4.6 (1H, m), 3.2 (2H, m), 2.2 (4H, m), 1.8 to 1.1 (60H, m), 0.86 (6H, t, J=6 Hz).

Preparation B-8

Starting from 3-hexadecanoyloxyoctadecanoic acid (400 mg) prepared by the method described in Preparation 2 and glycine (300 mg), N-(3-hexadecanoyloxyoctadecanoyl)glycine (260 mg) was obtained as powders according to a similar manner to that of Preparation B-1.

NMR (CDCl$_3$—CD$_3$OD, δ): 3.95 (2H, s), 2.5 (2H, d, J=7 Hz), 2.2 (2H, t, J=7 Hz), 1.9 to 1.1 (60H, m), 0.95 (6H, t, J=7 Hz).

EXAMPLE 1

To tert-butyl 15-methyl-3-(13-methyltetradecanoyloxy)hexadecanoate (2.95 g) prepared by the method described in Preparation A-1 (2) was added trifluoroacetic acid (10 ml) and the mixture was stirred at ambient temperature for 1 hour. Excess trifluoroacetic acid was distilled off under reduced pressure. Dry benzene was added to the residue and the solvent was evaporated off. This operation was repeated three times. After drying up completely by using high vacuum pump, the residue (15-methyl-3-(13-methyltetradecanoyloxy)hexadecanoic acid) was dissolved in ethyl acetate (100 ml) and N-hydroxysuccinimide (600 mg) was added. To the stirred mixture was added N,N'-dicyclohexylcarbodiimide (1.08 g) at 0° C.

The resulting mixture was stirred at ambient temperature overnight. The reaction mixture was filtered to remove N,N'-dicyclohexylurea and the filtrate was concentrated. The residue was dissolved in tetrahydrofuran (150 ml). The solution was added to a solution of N-L-valyl-L-glutamic acid (3.2 g) and triethylamine (3.63 ml) in water (300 ml).

The resulting mixture was stirred at ambient temperature for 5 hours. The reaction mixture was acidified with 1N hydrochloric acid, extracted with ethyl acetate, washed with brine and dried over magnesium sulfate. Ethyl acetate was evaporated off to give crude products which were subjected to column chromatography on silica gel (Merck) and eluted with a mixture of chloroform and methanol (7:3). The fractions containing the object compound were combined and concentrated under reduced pressure. The residue was dried up by high vacuum pump to afford powder of N-[N-[15-methyl-3-(13-methyltetradecanoyloxy)hexadecanoyl]-L-valyl]-L-glutamic acid (610 mg).

IR (CHCl$_3$): 3350, 2950, 2880, 1720, 1650 cm$^{-1}$.

NMR (CDCl$_3$—CD$_3$OD, $\delta$): 5.2 (1H, m), 4.4 to 4.1 (2H, m), 2.6 to 2.0 (6H, m), 1.8 to 1.1 (47H, m), 0.9 (18H, m).

EXAMPLE 2

To a solution of N-(3-hexadecanoyloxyoctadecanoyl)-L-valine (954 mg) prepared by the method of Preparation B-1 in dioxane (7 ml) were added N-hydroxysuccinimide (172 mg) and dicyclohexylcarbodiimide (321 mg). The mixture was stirred overnight at room temperature. The crystallized N,N'-dicyclohexylurea was removed by filtration, and the filtrate was concentrated under reduced pressure. To the residue was added a solution of dibenzyl L-glutamate (446 mg) in dimethoxyethane (15 ml) and the mixture was stirred at room temperature for 2 hours and then allowed to stand over-night. Water was added, and the appeared crystals were collected by filtration and washed with an aqueous sodium bicarbonate solution, water, 1N-hydrochloric acid solution and then water. The collected crystals were recrystallized from ethanol to give crystals of dibenzyl N-[N-(3-hexadecanoyloxyoctadecanoyl)-L-valyl]-L-glutamate (1.1 g).

IR (CHCl$_3$): 2920, 2850, 1730, 1660 cm$^{-1}$.

NMR (CDCl$_3$, $\delta$): 7.45 (10H, m), 5.25 (2H, s), 5.18 (2H, s), 4.5 (2H, m), 2.4 (6H, m), 1.8 to 1.2 (63H, m), 0.9 (12H, m).

EXAMPLE 3

Dibenzyl N-[N-(3-hexadecanoyloxyoctadecanoyl)-L-valyl]-L-glutamate (950 mg) prepared by the method of Example 2 was dissolved in a mixture of ethyl acetate (200 ml) and methanol (50 ml). A suspended mixture of palladium black (800 mg) in water (10 ml) was added thereto. The mixture was subjected to catalytic hydrogenation at 2.5 atmospheric pressure. The reaction mixture was filtered and the filtrate was concentrated under reduced pressure. The residue was dried up by using high vacuum pump to afford amorphus N-[N-(3-hexadecanoyloxyoctadecanoyl)-L-valyl]-L-glutamic acid (770 mg).

IR (CHCl$_3$): 3300, 2920, 2850, 1720, 1650 cm$^{-1}$.

NMR (CDCl$_3$—CD$_3$OD, $\delta$): 5.2 (1H, m), 4.5 (1H, m), 2.5 to 2.0 (6H, m), 1.8 to 1.1 (57H, m), 0.9 (12H, m).

EXAMPLE 4

To a solution of N-[N-(3-hexadecanoyloxyoctadecanoyl-L-valyl]-L-glutamic acid (100 mg) in methanol (5 ml) was added an ethereal solution of excess diazomethane. The resulting solution was allowed to keep in refrigerator over night. After an addition of 1 drop of acetic acid, the solvent was evaporated off to give a residue which was dried up by high vacuum pump to afford powder of dimethyl N-[N-(3-hexadecanoyloxyoctadecanoyl)-L-valyl]-L-glutamate (100 mg).

IR (CHCl$_3$): 2940, 2850, 1725, 1660 cm$^{-1}$.

NMR (CDCl$_3$, $\delta$): 7.05 (1H, m), 6.5 (1H, m), 5.2 (1H, m), 4.6 to 4.2 (2H, m), 3.74 (3H, s), 3.68 (3H, s), 2.5 to 2.1 (6H, m), 1.8 to 1.1 (57H, m), 0.95 (12H, m).

EXAMPLE 5

Starting from N-(2-hexadecanoyloxyhexadecanoyl)-L-valine (2.4 g) prepared by the method of Preparation B-2 and dibenzyl L-glutamate (1.26 g), dibenzyl N-[N-(2-hexadecanoyloxyhexadecanoyl)-L-valyl]-L-glutamate (3.2 g) was obtained as crystals according to a similar manner to that of Example 2. M.p. 65° C.

IR (CHCl$_3$): 3550, 2950, 2870, 1728, 1670 cm$^{-1}$.

NMR (CDCl$_3$, $\delta$): 7.4 (10H, s), 6.8 (2H, m), 5.2 (1H, m), 5.21 (2H, s), 5.15 (2H, s), 4.7 (1H, m), 4.3 (1H, m), 2.3 (4H, m), 1.9 to 1.1 (55H, m), 0.9 (12H, m).

EXAMPLE 6

Starting from dibenzyl N-[N-(2-hexadecanoyloxyhexadecanoyl)-L-valyl]-L-glutamate (3 g) prepared by the method described in Example 5, N-[N-(2-hexadecanoyloxyhexadecanoyl)-L-valyl]-L-glutamic acid (2.15 g) was obtained as crystals according to a similar manner to that of Example 3. M.p. 101°-3° C.

IR (CHCl$_3$): 3350, 2950, 2860, 1720, 1660 cm$^{-1}$.

NMR (CDCl$_3$—CD$_3$OD, $\delta$): 5.1 (1H, t, J=7 Hz), 4.5 (1H, m), 4.35 (1H, m), 2.6 to 2.1 (4H, m), 2.0 to 1.1 (55H, m), 0.9 (12H, m).

EXAMPLE 7

Starting from N-[3-(9-octadecenoyloxy)-11-eicosenoyl]-L-valine (2.7 g) and L-glutamic acid (2.2 g), N-[N-[3-(9-octadecenoyloxy)-11-eicosenoyl]-L-valyl]-L-glutamic acid (1.0 g) was obtained as powder according to a similar manner to that of Example 2.

IR (Nujol): 3300, 2925, 2850, 1720, 1650 cm$^{-1}$.

NMR (CDCl$_3$—CD$_3$OD, $\delta$): 5.3 (4H, t), 5.2 (1H, m), 4.6 to 4.4 (2H, m), 2.6 to 2.1 (6H, m), 2.1 to 1.8 (8H, m), 1.7 to 1.0 (49H, m), 0.9 (6H, t, J=6 Hz), 0.9 (6H, d, J=6 Hz).

EXAMPLE 8

(1) To tert-butyl 3-hexadecanoyloxyoctadecanoate (16.56 g) was added trifluoroacetic acid (20 ml) and the mixture was stirred at room temperature for 1 hour. Trifluoroacetic acid was removed off under reduced pressure, and to the residue was added dry benzene, followed by evaporation of the solvent. This operation was repeated three times. To a solution of the dried residue in ethyl acetate (250 ml) were added N-hydroxysuccinimide (3.21 g) and N,N'-dicyclohexylcarbodiimide (5.75 g). The mixture was stirred at ambient temperature overnight and then filtered to remove N,N'-dicyclohexylurea. The filtrate was condensed and dried up by high vacuum pump to give N-hydroxysuccinimide ester of 3-hexadecanoyloxyoctadecanoic acid (16.2 g).

(2) To a solution of N-hydroxysuccinimide ester of 3-hexadecanoyloxyoctadecanoic acid (1.5 g) in tetrahydrofuran (100 ml) were added a solution of N-(L-threonyl)-L-glutamic acid (0.79 g) and triethylamine (0.88 ml) in water (220 ml). The resulting mixture was stirred at ambient temperature overnight. The reaction mixture was acidified with 1N hydrochloric acid, extracted with ethyl acetate, washed with water and dried over magnesium sulfate. Ethyl acetate was distilled off to give a residue which was purified by silica gel column chromatography. Elution with chloroform-methanol (20:1) afforded powder of N-[N-(3-hexadecanoyloxyoctadecanoyl)-L-threonyl]-L-glutamic acid (1.0 g).

IR (CHCl$_3$): 3280, 1720, 1660 cm$^{-1}$.

EXAMPLE 9

Starting from N-[N-(3-hexadecanoyloxyoctadecanoyl)-β-alanyl]-L-threonine (450 mg) prepared by the method of Preparation B-4 and dibenzyl L-glutamate (210 mg), dibenzyl N-[N-[N-(3-hexadecanoyloxyoctadecanoyl)-β-alanyl]-L-threonyl]-L-glutamate (250 mg) was obtained as crystals according to a similar manner to that of Example 2.

IR (CHCl$_3$): 3400, 2940, 2860, 1725, 1660 cm$^{-1}$.

NMR (CDCl$_3$, δ): 7.4 (10H, m), 5.2 (1H, m), 5.2 (2H, s), 5.13 (2H, s), 4.5 (1H, m), 3.5 (2H, m), 2.45 (8H, m), 1.8 to 1.1 (59H, m), 0.95 (6H, t, J=6 Hz).

EXAMPLE 10

Starting from dibenzyl N-[N-[N-(3-hexadecanoyloxyoctadecanoyl)-β-alanyl]-L-threonyl]-L-glutamate (190 mg), N-[N-[N-(3-hexadecanoyloxyoctadecanoyl)-β-alanyl]-L-threonyl]-L-glutamic acid (130 mg) was obtained as crystals according to a similar manner to that of Example 3. M.p. 150°–153° C.

IR (CHCl$_3$): 3400, 2940, 2860, 1720, 1660 cm$^{-1}$.

NMR (CDCl$_3$—CD$_3$OD, δ): 5.2 (1H, m), 4.4 (3H, m), 3.5 (2H, m), 2.5 (8H, m), 1.9 to 1.1 (59H, m), 0.95 (6H, t, J=6 Hz).

EXAMPLE 11

N-(3-hexadecanoyloxyoctadecanoyl)-β-alanine (1.47 g) prepared by the method of Preparation B-5 and N,N'-dicyclohexylcarbodiimide (412 mg) were added to a mixed solution of dichloromethane (20 ml) and dioxane (20 ml). The resulting mixture was stirred for 15 minutes. Then, a solution of dibenzyl L-glutamate (650 mg) in dioxane (10 ml) was added thereto over a period of 30 minutes. The mixture was stirred for 2 hours at room temperature and allowed to stand overnight. The precipitated N,N'-dicyclohexylurea was removed off by filtration, and the filtrate was concentrated under reduced pressure. The residue was recrystallized from ethanol to afford crystals of dibenzyl N-[N-(3-hexadecanoyloxyoctadecanoyl)-β-alanyl]-L-glutamate (850 mg).

IR (CHCl$_3$): 3400, 3300, 2940, 2860, 1730, 1660 cm$^{-1}$.

NMR (CDCl$_3$, δ): 7.4 (10H, m), 5.2 (2H, s), 5.15 (1H, m), 5.14 (2H, s), 4.65 (1H, m), 3.6 (2H, m), 2.5 to 2.1 (8H, m), 1.9 to 1.1 (56H, m), 0.95 (6H, t, J=6 Hz).

EXAMPLE 12

Starting from dibenzyl N-[N-(3-hexadecanoyloxyoctadecanoyl)-β-alanyl]-L-glutamate (770 mg), N-[N-(3-hexadecanoyloxyoctadecanoyl)-β-alanyl]-L-glutamic acid (400 mg) was obtained as crystals according to a similar manner to that of Example 3. M.p. 100°–104° C.

IR (CHCl$_3$): 3350, 2940, 2860, 1720, 1660 cm$^{-1}$.

NMR (CDCl$_3$—CD$_3$OD, δ): 5.2 (1H, m), 4.6 (1H, m), 3.4 (2H, m), 2.4 (8H, m), 1.9 to 1.1 (56H, m), 0.95 (6H, t, J=6 Hz).

EXAMPLE 13

Starting from N-(3-hexadecanoyloxyoctadecanoyl)-5-aminopentanoic acid (1.27 g) prepared by the method of Preparation B-6 and dibenzyl L-glutamate (0.65 g), dibenzyl N-[N-(3-hexadecanoyloxyoctadecanoyl)-5-aminopentanoyl]-L-glutamate (1.5 g) was obtained as crystal according to a similar manner to that of Example 2.

IR (CHCl$_3$): 3400, 2940, 2860, 1725, 1660 cm$^{-1}$.

NMR (CDCl$_3$, δ): 7.4 (10H, m), 6.4 (1H, m), 6.0 (1H, m), 5.2 (1H, m), 5.22 (2H, s), 5.15 (2H, s), 4.6 (1H, m), 3.2 (2H, m), 2.5 to 2.0 (8H, m), 1.9 to 1.1 (60H, m), 0.95 (6H, t, J=6 Hz).

EXAMPLE 14

Starting from dibenzyl N-[N-(3-hexadecanoyloxyoctadecanoyl)-5-aminopentanoyl]-L-glutamate (1.5 g) prepared by the method described in Example 12, N-[N-(3-hexadecanoyloxyoctadecanoyl)-5-aminopentanoyl]-L-glutamic acid (1.08 g) was obtained as crystals according to a similar manner to that of Example 3. M.p. 108°–9° C.

IR (CHCl$_3$): 3300, 2940, 2860, 1720, 1660 cm$^{-1}$.

NMR (CDCl$_3$, δ): 5.2 (1H, m), 4.6 (1H, m), 3.3 (2H, m), 2.6 to 2.05 (8H, m), 1.9 to 1.1 (60H, m), 0.95 (6H, t, J=6 Hz).

EXAMPLE 15

Starting from N-hydroxysuccinimide ester of 3-hexadecanoyloxyoctadecanoic acid (10.5 g) prepared by the method of Example 8(1) and Oγ-benzyl-L-glutamic acid (11.4 g), Nα-(3-hexadecanoyloxyoctadecanoyl)-Oγ-benzyl-L-glutamic acid (8.76 g) was obtained as powder according to a similar manner to that of Example 8(2).

EXAMPLE 16

(1) To a solution of N-(3-hexadecanoyloxyoctadecanoyl)-L-phenylalanine (0.9 g) prepared by the method of Preparation B-7 in ethyl acetate (10 ml) were added N-hydroxysuccinimide (0.16 g) and N,N'-dicyclohexylcarbodiimide (0.28 g). The mixture was stirred at ambient temperature overnight and then filtered to remove N,N'-dicyclohexylurea. The filtrate was concentrated and dried up by high vacuum pump to give N-hydroxysuccinimide ester of N-(3-hexadecanoyloxyoctadecanoyl)-L-phenylalanine (0.88 g) as powder.

(2) To a solution of N-hydroxysuccinimide ester of N-(3-hexadecanoyloxyoctadecanoyl)-L-phenylalanine (0.88 g) in tetrahydrofuran (10 ml) was added a solution of Oγ-benzyl-L-glutamic acid (0.5 g) and a 1N sodium hydroxide solution (2 ml) at 0° C. The resulting mixture was reached to room temperature and stirred at ambient temperature overnight. The reaction mixture was acidified with 1N hydrochloric acid, extracted with ethyl acetate, washed with water and dried over magnesium sulfate. Ethyl acetate was distilled off to give a residue which was purified by silica gel column chromatography. Elution with a mixture of chloroform and methanol (9:1) afforded an oil of Nα-[N-(3-hexadecanoyloxyoctadecanoyl)-L-phenylalanyl]-Oγ-benzyl-L-glutamic acid (0.8 g).

EXAMPLE 17

Starting from Nα-[N-(3-hexadecanoyloxyoctadecanoyl)-L-phenylalanyl]-Oγ-benzyl-L-glutamic acid (0.8 g) prepared by the method described in Example 16 (2), N-[N-(3-hexadecanoyloxyoctadecanoyl)-L-phenylalanyl]-L-glutamic acid (0.5 g) was obtained as powders according to a similar manner to that of Example 3.

IR (Nujol): 3300, 2925, 2850, 1720, 1650 cm$^{-1}$.

NMR (CDCl$_3$—CD$_3$OD, δ): 7.3 (5H, s), 5.2 (1H, m), 4.7 to 4.5 (2H, m), 3.1 (2H, d), 2.6 to 2.1 (6H, m), 2.1 to 1.1 (56H, m), 0.9 (6H, t, J=6 Hz).

EXAMPLE 18

Starting from 3-hexadecanoyloxyoctadecanoic acid (150 mg) prepared by the method described in Preparation A-2 (5) and N-(β-alanyl)-L-aspartic acid (150 mg), N-[N-(3-hexadecanoyloxyoctadecanoyl)-β-alanyl]-L-aspartic acid (50 mg) was obtained as powder according to a similar manner to that of Example 2.

NMR (CDCl$_3$—CD$_3$OD, δ): 5.2 (1H, m), 4.76 (1H, m), 3.5 (2H, m), 2.85 (2H, d, J=5 Hz), 2.4 (6H, m), 1.8 to 1.1 (60H, m), 0.9 (6H, t, J=6 Hz).

EXAMPLE 19

(1) Starting from N$^α$-(3-hexadecanoyloxyoctadecanoyl)-O$^γ$-benzyl-L-glutamic acid (1.1 g) prepared by the method described in Example 15 and O$^γ$-benzyl-L-glutamic acid (0.57 g), N$^α$-[N$^α$-(3-hexadecanoyloxyoctadecanoyl)-O$^γ$-benzyl-L-glutamyl]-O$^γ$-benzyl-L-glutamic acid was obtained according to a similar manner to that of Example 2.

(2) Starting from N$^α$-[N$^α$-(3-hexadecanoyloxyoctadecanoyl)-O$^γ$-benzyl-L-glutamyl]-O$^γ$-benzyl-L-glutamic acid above prepared, N-[N-(3-hexadecanoyloxyoctadecanoyl)-L-glutamyl]-L-glutamic acid (570 mg) was obtained as powder according to a similar manner to that of Example 3.

IR (CHCl$_3$): 3350, 2950, 2880, 1720, 1650 cm$^{-1}$.

NMR (CDCl$_3$—CD$_3$OD, δ): 5.2 (1H, m), 4.4 (2H, m), 1.9 to 2.7 (8H, m), 1.8 to 1.0 (58H, m), 0.9 (6H, t, J=6 Hz).

EXAMPLE 20

(1) Starting from N$^α$-(3-hexadecanoyloxyoctadecanoyl)-N$^ε$-benzyloxycarbonyl-L-lysine (8.5 g) prepared by the method described in Preparation B-8 and N-hydroxysuccinimide (1.3 g), N-hydroxysuccinimide ester of N$^α$-(3-hexadecanoyloxyoctadecanoyl)-N$^ε$-benzyloxycarbonyl-L-lysine (9.0 g) was obtained as powder according to a similar manner to that of Example 16(1).

(2) Starting from N-hydroxysuccinimide ester of N$^α$-(3-hexadecanoyloxyoctadecanoyl)-N$^ε$-benzyloxycarbonyl-L-lysine (3 g) prepared above and L-glutamic acid (1.18 g), N-[N$^α$-(3-hexadecanoyloxyoctadecanoyl)-N$^ε$-benzyloxycarbonyl-L-lysyl]-L-glutamic acid (2.4 g) was obtained as crystals according to a similar manner to that of Example 16(2).

EXAMPLE 21

N-[N$^α$-(3-hexadecanoyloxyectadecanoyl)-N$^ε$-benzyloxycarbonyl-L-lysyl]-L-glutamic acid (2.4 g) was added to a 30% hydrogen bromide-acetic acid solution (15 ml) at 0° C. and the mixture was stirred at room temperature for 1 hour. To the reaction mixture was added n-hexane and the precipitate was collected by filtration, and dried to give N-[N-(3-hexadecanoyloxyoctadecanoyl)-L-lysyl]-L-glutamic acid (1.4 g) as powder.

IR (Nujol): 3300, 2925, 2850, 1720, 1650 cm$^{-1}$.

NMR (CDCl$_3$—CD$_3$OD, δ): 5.2 (1H, m), 4.5 to 4.2 (2H, m), 3.3 to 3.0 (2H, m), 2.6 to 2.1 (6H, m), 2.1 to 1.1 (62H, m), 0.9 (6H, t, J=6 Hz).

EXAMPLE 22

A solution of dibenzyl N-(N-tert-butoxycarbonyl-L-valyl)-L-glutamate (1 g) and anisole (0.5 ml) in trifluoroacetic acid (2 ml) was stirred at 0° C. for 1 hour. Evaporation of trifluoroacetic acid under reduced pressure gave a residue which was taken up in benzene. Benzene was distilled off by using high vacuum pump. This operation was repeated three times to leave crude dibenzyl N-L-valyl-L-glutamate, which was dissolved in chloroform (20 ml). To this solution were added triethylamine (3 ml) and butyric anhydride (0.5 ml) and the resulting mixture was stirred at room temperature for 4 hours. The reaction mixture was poured into ice water and the separated organic layer was washed with dilute hydrochloric acid solution, a saturated aqueous solution of sodium bicarbonate and brine respectively. After solvent was evaporated, the residue was recrystallized from petroleum ether to afford dibenzyl N-(N-butanoyl-L-valyl)-L-glutamate (613 mg) as crystals.

IR (CHCl$_3$): 3425, 2970, 1730, 1655, 1245, 1170, 695 cm$^{-1}$.

NMR (CDCl$_3$, δ): 7.30 (10H, s), 6.73 (1H, m), 6.07 (1H, m), 5.10 (2H, s), 5.05 (2H, s), 4.76 to 4.03 (2H, m), 2.50 to 1.23 (9H, m), 0.9 (9H, m).

EXAMPLE 23

A mixture of dibenzyl N-(N-butanoyl-L-valyl)-L-glutamate (613 mg) and palladium black (50 mg) in methanol (50 ml) was subjected to catalytic hydrogenation under atmospheric pressure. After the reaction mixture was filtered, the filtrate was concentrated under reduced pressure to give a residue which was recrystallized from petroleum ether to afford N-(N-butanoyl-L-valyl)-L-glutamic acid as crystals (343 mg).

IR (CHCl$_3$): 3350, 3325, 2900, 1725, 1625, 1260, 1175 cm$^{-1}$.

NMR (CD$_3$OD, δ): 4.43 (1H, m), 4.17 (1H, d, J=7 Hz), 2.57 to 1.33 (9H, m), 0.98 (9H, m).

EXAMPLE 24

A solution of dibenzyl N-(N-tert-butoxycarbonyl-L-valyl)glutamate (1 g) and anisole (1 ml) in trifluoroacetic acid (2 ml) was stirred at 0° C. for 1 hour. Evaporation of trifluoroacetic acid under reduced pressure gave a residue which was taken up in benzene. Benzene was distilled off by using high vacuum pump. This operation was repeated three times to leave crude dibenzyl N-(L-valyl)-L-glutamate, which was dissolved in tetrahydrofuran (20 ml). To this solution was added triethylamine (1 ml) and n-octanoyl chloride (0.7 ml) at 0° C., and the resulting mixture was stirred at room temperature for 1 hour. The reaction mixture was diluted with chloroform and the organic layer was washed with 1N hydrochloric acid solution, aqueous sodium carbonate solution and brine successively, dried over magnesium sulfate. After solvent was evaporated, the residue was crystallized from ethyl acetate to afford white amorphous powder of dibenzyl N-(N-octanoyl-L-valyl)-L-glutamate (600 mg).

IR (CHCl$_3$): 3420, 3300, 2960, 2930, 1730, 1660, 1500, 690 cm$^{-1}$.

NMR (CDCl$_3$, δ): 7.33 (10H, s), 6.97 (1H, d, J=8 Hz), 6.17 (1H, d, J=8 Hz), 5.13 (2H, s), 5.07 (2H, s), 4.67 (1H, m), 4.33 (1H, m), 2.4 to 2.0 (7H, m), 1.4 to 1.2 (10H, m), 0.9 (9H, m).

EXAMPLE 25

Starting from dibenzyl N-(N-octanoyl-L-valyl)-L-glutamate (600 mg) prepared by the method of Example 24, N-(N-octanoyl-L-valyl)-L-glutamic acid (350 mg) was obtained as white powder according to a similar manner to that of Example 23.

IR (Nujol): 3350, 1740, 1715, 1660 cm$^{-1}$.

NMR (CD$_3$OD, $\delta$): 4.47 (1H, m), 4.20 (1H, m), 2.5 to 2.0 (7H, m), 1.5 to 1.2 (10H, m), 0.98 (9H, m).

EXAMPLE 26

Starting from dibenzyl N-(N-tert-butoxycarbonyl-L-valyl)-L-glutamate (1 g) and hexadecanoyl chloride (620 mg), dibenzyl N-(N-hexadecanoyl-L-valyl)-L-glutamate (800 mg) was obtained as crystals according to a similar manner to that of Example 24.

IR (CHCl$_3$): 3410, 3300, 2920, 2850, 1730, 1660 cm$^{-1}$.

NMR (CDCl$_3$, $\delta$): 7.3 (10H, s), 6.7 (1H, d, J=8 Hz), 6.2 (1H, d, J=8 Hz), 5.2 (2H, s), 5.15 (2H, s), 4.8 to 4.2 (2H, m), 2.6 to 2.0 (7H, m), 1.6 to 1.1 (26H, m), 1.0 to 0.9 (9H, m).

EXAMPLE 27

Starting from dibenzyl N-(N-hexadecanoyl-L-valyl)-L-glutamate (600 mg) prepared by the method of Example 26, N-(N-hexadecanoyl-L-valyl)-L-glutamate (300 mg) was obtained as crystals according to a similar manner to that of Example 23.

IR (Nujol): 3300, 2910, 2850, 1735, 1700, 1640 cm$^{-1}$.

NMR (CDCl$_3$—CD$_3$OD, $\delta$): 4.5 (1H, m), 4.1 (1H, m), 2.5 to 1.9 (7H, m), 1.8 to 1.0 (26H, m), 1.0 to 0.8 (9H, m).

EXAMPLE 28

A mixture of docosanoic acid (500 mg) and thionyl chloride (2 ml) in benzene (5 ml) was refluxed for 1 hour. After removal of the solvent under reduced pressure, the residue was taken up in benzene and benzene was evaporated off. This operation was repeated three times to give crude docosanoyl chloride. Meanwhile, a solution of dibenzyl N-(N-tert-butoxycarbonyl-L-valyl)-L-glutamate (773 mg) and anisole (0.25 ml) in trifluoroacetic acid (1 ml) was stirred at 0° C. for 1 hour. Evaporation of trifluoroacetic acid under reduced pressure gave a residue which was taken up in benzene. Benzene was distilled off by using a high vacuum pump. This operation was repeated three times to leave crude dibenzyl N-(L-valyl)-L-glutamate, which was dissolved in tetrahydrofuran (5 ml). To this solution were added triethylamine (0.7 ml) and a solution of docosanoyl chloride prepared as mentioned above in tetrahydrofuran (3 ml). After the resulting mixture was stirred at room temperature for 3 hours, the solvent was removed under reduced pressure, and the residue was dissolved in chloroform. The chloroform solution was washed with 1N sodium hydroxide solution, 1N hydrochloric acid solution, and an aqueous solution of sodium bicarbonate successively, and then dried over magnesium sulfate. After evaporation of the solvent, the residue was purified by being subjected to a silica gel column chromatography. Elution with chloroform and an usual work-up afforded dibenzyl N-(N-docosanoyl-L-valyl)-L-glutamate (520 mg, powder).

IR (CHCl$_3$): 3415, 3300, 2960, 2930, 1730, 1660 cm$^{-1}$.

NMR (CDCl$_3$, $\delta$): 7.3 (10H, s), 6.9 (1H, d, J=8 Hz), 6.12 (1H, d, J=8 Hz), 5.15 (2H, s), 5.05 (2H, s), 4.6–4.05 (2H, m), 2.6–1.9 (7H, m), 1.6–1.06 (38H, m), 0.93 (9H, m).

EXAMPLE 29

Starting from dibenzyl N-(N-docosanoyl-L-valyl)-L-glutamate (500 mg) prepared by the method of Example 28, N-(N-docosanoyl-L-valyl)-L-glutamic acid (300 mg) was obtained as powder according to a similar manner to that of Example 23.

IR (Nujol): 3350, 3325, 1730, 1695, 1635 cm$^{-1}$.

NMR (CDCl$_3$: CD$_3$OD=1: 1, $\delta$): 4.45 (1H, m), 4.17 (1H, d, J=7 Hz), 2.6 to 1.9 (7H, m), 1.6 to 1.06 (38H, m), 0.93 (9H, m).

EXAMPLE 30

Starting from triacontanoic acid (452 mg) and dibenzyl N-(N-tert-butoxycarbonyl-L-valyl)-L-glutamate (526 mg), dibenzyl N-(N-triacontanoyl-L-valyl)-L-glutamate (430 mg) was obtained as powder according to a similar manner to that of Example 28.

IR (CHCl$_3$): 3410, 3300, 2960, 2930, 1730, 1660 cm$^{-1}$.

NMR (CDCl$_3$, $\delta$): 7.3 (10H, s), 6.9 (1H, d, J=8 Hz), 6.15 (1H, d, J=8 Hz), 5.15 (2H, s), 5.05 (2H, s), 4.6 to 4.05 (2H, m), 2.6 to 1.9 (7H, m), 1.6 to 1.02 (56H, m), 0.93 (9H, m).

EXAMPLE 31

Starting from dibenzyl N-(N-triacontanoyl-L-valyl)-L-glutamate (400 mg) prepared by the method of Example 30, N-(N-triacontanoyl-L-valyl)-L-glutamic acid (240 mg) was obtained as powder according to a similar manner to that of Example 23.

IR (Nujol): 3350, 3325, 1730, 1695, 1635 cm$^{-1}$.

NMR (CDCl$_3$: CD$_3$OD=1: 1, $\delta$): 4.5 (1H, m), 4.17 (1H, d, J=7 Hz), 2.6 to 1.9 (7H, m), 1.6 to 1.05 (56H, m), 0.93 (9H, m).

EXAMPLE 32

To a solution of N-(3-hexadecanoyloxyoctadecanoyl)-L-valine (1.72 g) prepared by the method of Preparation B-1 in dioxane (13 ml) were added N-hydroxysuccinimide (310 mg) and N,N'-dicyclohexylcarbodiimide (579 mg), and the mixture was stirred overnight at room temperature. The appeared N,N'-dicyclohexylurea was removed by filtration and the filtrate was condensed under reduced pressure. To a solution of the residue in dimethylformamide (45 ml) was added a solution of N$^\epsilon$-benzyloxycarbonyl-L-lysine (2.06 g) in 1N NaOH (7 ml) and water (30 ml) at 0° C. The mixture was stirred at room temperature for one hour. The precipitated solid was collected by filtration, washed with petroleum ether, dissolved in a mixture of ethyl acetate and 1N hydrochloric acid. Ethyl acetate layer was washed with water, and evaporation of the solvent gave a residue (1.9 g) which was purified by column chromatography on silica gel and eluted with a mixture of chloroform and methanol (9:1). The fractions containing the object compound were combined and concentrated under reduced pressure. The residue was dried up by high vacuum pump to afford a powder of N$^\alpha$-[N-(3-hexadecanoyloxyoctadecanoyl)-L-valyl]-N$^\epsilon$-benzyloxycarbonyl-L-lysine (1 g).

NMR (CDCl$_3$, $\delta$): 7.3 (5H, s), 5.2 (1H, m), 5.1 (2H, s), 4.5 (2H, m), 2.4 (2H, m), 3.1 (2H, m), 2.2 (2H, m), 1.8 to 1.0 (61H, m), 0.86 (12H, m).

EXAMPLE 33

To N$^\alpha$-[N-(3-hexadecanoyloxyoctadecanoyl)-L-valyl]-N$^\epsilon$-benzyloxycarbonyl-L-lysine (650 mg) in acetic acid (5 ml) was added 30% hydrogen bromide solution in acetic acid (4 ml), and the mixture was stirred at room temperature for 2 hours. Excess solvent was removed off by evaporation under reduced pressure. The residue was taken up in benzene, and the solvent was distilled off. This operation was repeated twice to give powder of N-[N-(3-hexadecanoyloxyoctadecanoyl)-L-valyl]-L-lysine.hydrogen bromide (550 mg).

IR (CHCl$_3$): 3300, 2920, 2850, 1720, 1640 cm$^{-1}$.

NMR (CDCl$_3$—CD$_3$OD, δ): 5.2 (1H, m), 4.4 (2H, m), 3.0 (2H, m), 2.6 to 2.2 (4H, m), 1.8 to 1.1 (64H, m), 0.95 (12H, m).

EXAMPLE 34

To a solution of N-hydroxysuccinimide ester of 3-hexadecanoyloxyoctadecanoic acid (7.5 g) prepared by the method of Example 8 (1) in dimethylformamide (200 ml) was added a solution of N$^\epsilon$-benzyloxycarbonyl-L-lysine (6.6 g) in 1N sodium hydroxide (23.6 ml) at room temperature. The mixture was stirred at ambient temperature for 3 hours. The precipitated solid was collected by filtration and the filtrate was concentrated under reduced pressure. The solid and the residue was combined. Then, the mixture was acidified with dilute hydrochloric acid and extracted with ethyl acetate. The organic layer was washed with water. The ethyl acetate solution was dried over magnesium sulfate, and then concentrated to give a residue which was dried up by high vacuum pump to afford powder of N$^\alpha$-(3-hexadecanoyloxyoctadecanoyl)-N$^\epsilon$-benzyloxycarbonyl-L-lysine (8.5 g).

EXAMPLE 35

Starting from N-hydroxysuccinimide ester of N$^\alpha$-(3-hexadecanoyloxyoctadecanoyl)-N$^\epsilon$-benzyloxycarbonyl-L-lysine (3 g) prepared by the method described in Example 20 (1), and N$^\epsilon$-benzyloxycarbonyl-L-lysine (2.24 g), N$^\alpha$-[N$^\alpha$-(3-hexadecanoyloxyoctadecanoyl)-N$^\epsilon$-benzyloxycarbonyl-L-lysyl]-N$^\epsilon$-benzyloxycarbonyl-L-lysine (2.7 g) was obtained as crystals according to a similar manner to that of Example 16 (2).

EXAMPLE 36

To N$^\alpha$-[N$^\alpha$-(3-hexadecanoyloxyoctadecanoyl)-N$^\epsilon$-benzyloxycarbonyl-L-lysyl]-N$^\epsilon$-benzyloxycarbonyl-L-lysine (2.7 g) prepared by the method of Example 32 was added 30% HBr-acetic acid solution (15 ml), and the mixture was stirred at room temperature for one hour. To the reaction mixture was added hexane and the precipitate was collected by filtration and dried to give N-[N-(3-hexadecanoyloxyoctadecanoyl)-L-lysyl]-L-lysine dihydrogen bromide (1.7 g).

IR (Nujol): 3300, 2940, 2850, 1720, 1650 cm$^{-1}$.

NMR (CDCl$_3$—CD$_3$OD, δ): 5.2 (1H, m), 4.4 to 4.7 (2H, m), 3.0 to 3.3 (4H, m), 2.1 to 2.6 (4H, m), 1.1 to 2.1 (66H, m), 0.9 (6H, t, J=6 Hz).

EXAMPLE 37

Starting from N-(3-hexadecanoyloxyoctadecanoyl)-L-valine (1.28 g) and taurine (1 g), N-[N-(3-hexadecanoyloxyoctadecanoyl)-L-valyl]taurine (400 mg) was obtained as powder according to a similar manner to that of Example 32.

IR (CHCl$_3$): 3400, 2940, 2860, 1720, 1650 cm$^{-1}$.

NMR (CDCl$_3$—CD$_3$OD, δ): 5.2 (1H, m), 4.2 (1H, m), 3.7 (2H, m), 3.1 (2H, m), 2.6 to 2.1 (4H, m), 1.9 to 1.2 (57H, m), 0.95 (12H, m).

EXAMPLE 38

Starting from N-(3-hexadecanoyloxyoctadecanoyl)glycine (1.19 g) prepared by the method of Preparation B-8 and taurine (0.25 g), N-[N-(3-hexadecanoyloxyoctadecanoyl)glycyl]taurine (1.1 g) was obtained as crystals according to a similar manner to that of Example 37.

EXAMPLE 39

(1) Starting from N$^\alpha$-(3-hexadecanoyloxyoctadecanoyl)-O$^\gamma$-benzyl-L-glutamic acid (2 g) prepared by the method of Example 15, and L-threonine (0.94 g), N-[N$^\alpha$-(3-hexadecanoyloxyoctadecanoyl)-O$^\gamma$-benzyl-L-glutamyl]threonine was obtained.

(2) The whole amount of N-[N$^\alpha$-(3-hexadecanoyloxyoctadecanoyl)-O$^\gamma$-benzyl-L-glutamyl]threonine prepared above was dissolved in methanol (100 ml), and palladium black (200 mg) was added thereto. The mixture was subjected to catalytic hydrogenation at atmospheric pressure. The reaction mixture was filtered and the filtrate was concentrated under reduced pressure. The residue was dried up by using high vacuum pump to afford powder of N-[N-(3-hexadecanoyloxyoctadecanoyl)-L-glutamyl]-L-threonine (910 mg).

IR (CHCl$_3$): 3350, 2950, 2880, 1720, 1650 cm$^{-1}$.

NMR (CDCl$_3$—CD$_3$OD, δ): 5.2 (1H, m), 4.6 to 4.3 (3H, m), 2.7 to 2.0 (6H, m), 1.8 to 1.0 (59H, m), 0.9 (6H, t, J=6 Hz).

EXAMPLE 40

Starting from N$^\alpha$-(3-hexadecanoyloxyoctadecanoyl)-N$^\epsilon$-benzyloxycarbonyl-L-lysine (2.68 g) prepared by the method of Example 20 (1), and L-threonine (0.95 g), N-[N$^\alpha$-(3-hexadecanoyloxyoctadecanoyl)-N$^\epsilon$-benzyloxycarbonyl-L-lysyl]-L-threonine (2.4 g) was obtained as crystals according to a similar manner to that of Example 32.

EXAMPLE 41

N-[N$^\alpha$-(3-hexadecanoyloxyoctadecanoyl)-N$^\epsilon$-benzyloxycarbonyl-L-lysyl]-L-threonine (2.4 g) prepared by the method of Example 40 was dissolved in tetrahydrofuran (30 ml), and palladium black (0.3 g) added thereto. The mixture was subjected to catalytic hydrogenation at atmospheric pressure. The reaction mixture was filtered and the filtrate was concentrated under reduced pressure. The residue was purified by column chromatography on silica gel. Elution with a mixture of chloroform and methanol (50:1) afford powder of N-[N-(3-hexadecanoyloxyoctadecanoyl)-L-lysyl]-L-threonine (1.3 g).

IR (Nujol): 3300, 2925, 2850, 1720, 1650 cm$^{-1}$.

NMR (CDCl$_3$—CD$_3$OD, δ): 5.2 (1H, m), 4.5 to 4.2 (3H, m), 3.3 to 3.0 (2H, m), 2.6 to 2.1 (4H, m), 2.1 to 1.0 (63H, m), 0.9 (6H, t, J=6 Hz).

EXAMPLE 42

A solution of N-hydroxysuccinimide ester of 3-hexadecanoyloxyoctadecanoic acid (1.5 g) prepared by the method of Example 8 (1), L-threonyl-L-threonine (0.7 g) and triethylamine (0.44 ml) in tetrahydrofuran water (100 ml-200 ml) was stirred at room temperature for 5 hours. After removal of tetrahydrofuran under reduced pressure, the residue was acidified with 1% hydrochloric acid (100 ml) and extracted with ethyl acetate. The extract was washed with water, dried over magnesium sulfate, and concentrated to give a residue which was purified by column chromatography on silica gel. Elution with a mixture of chloroform and methanol (20:1) afforded N-[N-(3-hexadecanoyloxyoctadecanoyl)-L-threonyl]-L-threonine (1.2 ) as powder.

IR (CHCl$_3$): 3400–3300, 1720, 1650 cm$^{-1}$.

EXAMPLE 43

N-[N-(3-hexadecanoyloxyoctadecanoyl)-L-threonyl]-L-glutamic acid prepared by the method of Example 8 (2) (100 mg) was dissolved in methanol (10 ml) and excess etherial diazomethane solution was added thereto. After the mixture was allowed to stand at room temperature for one hour. The solvent was evaporated off under reduced pressure. The residue was purified by preparative thin layer chromatography and eluted with a mixture of chloroform and methanol (9:1) to give dimethyl N-[N-(3-hexadecanoyloxyoctadecanoyl)-L-threonyl]-L-glutamate (95 mg) as powder.

IR (CHCl$_3$): 3400, 2920, 2850, 1730, 1660 cm$^{-1}$.

NMR (CDCl$_3$, δ): 7.35 (1H, d, J=7 Hz), 6.75 (1H, d, J=7 Hz), 5.2 (1H, m), 4.8 to 4.2 (3H, m), 3.75 (3H, s), 3.67 (3H, s), 3.5 (1H, m), 2.8 to 1.9 (8H, m), 1.9 to 1.0 (57H, m), 0.9 (6H, t, J=6 Hz).

EXAMPLE 44

To a solution of 3-hexadecanoyloxyoctadecanoic acid (55 g) and triethylamine (16 ml) in tetrahydrofuran (500 ml) was added ethyl chloroformate (11 ml) dropwise with stirring at −20° C., and the mixture was stirred for 1 hour at the same temperature. To the mixture was added triethylamine (32 ml) and then, a solution of dibenzyl N-(L-threonyl)-L-glutamate (77 g) in tetrahydrofuran (100 ml) dropwise and the mixture was stirred for 3 hours at room temperature. Tetrahydrofuran was removed under reduced pressure to give the residue which was taken up in ethyl acetate. The ethyl acetate solution was washed with diluted hydrochloric acid and diluted sodium bicarbonate and dried. Evaporation of the solvent gave the residue which was recrystallized from ethanol to leave dibenzyl N-[N-(3-hexadecanoyloxyoctadecanoyl)-L-threonyl]-L-glutamate (79 g).

IR (CHCl$_3$): 3400, 2920, 2850, 1730, 1660, 1500, 1170, 695 cm$^{-1}$.

EXAMPLE 45

Dibenzyl N-[N-(3-hexadecanoyloxyoctadecanoyl)-L-threonyl]-L-glutamate (48 g) in demethylformamide (500 ml) was hydrogenated over palladium black (1 g) at room temperature at 1 atmospheric pressure. After the theoritical amount of hydrogen was adsorbed, dimethylformamide was removed under reduced pressure. The residual crude crystal was recrystallized from ethanol to give N-[N-(3-hexadecanoyloxyoctadecanoyl)-L-threonyl]-L-glutamic acid (35.5 g).

IR (CHCl$_3$): 3280, 1720, 1660 cm$^{-1}$.

NMR (CDCl$_3$—CD$_3$OD, δ): 5.2 (1H, m), 4.8 to 4.0 (3H, m), 2.7 to 2.1 (6H, m), 1.9 to 1.1 (59H, m), 0.9 (6H, t, J=7 Hz).

What we claim is:

1. A compound of the formula:

$$\begin{array}{c}R^1\\ \diagdown\\ \phantom{R^2}CH-A^1-CO-\left[NHCH-A^2-CO\right]-\\ \diagup\quad\quad\quad\quad\quad\quad\quad\quad |\\ R^2\quad\quad\quad\quad\quad\quad\quad\quad R^3\quad\quad\quad\quad_m\end{array}$$

-continued $$\left[NHCH-A^3-CO\right]_n-NHCHR^6$$
$$\quad\quad\, |\quad\quad\quad\quad\quad\quad\quad\quad\quad |$$
$$\quad\quad R^4\quad\quad\quad\quad\quad\quad\quad\quad R^5$$

wherein
$R^1$ is alkanoyloxy or alkenoyloxy;
$R^2$ is alkyl or alkenyl;
$R^3$ and $R^4$ are each hydrogen, lower alkyl, hydroxy(lower)alkyl, ar(lower)alkyl, esterified carboxy(lower)alkyl, carboxy(lower)alkyl, protected amino(lower)alkyl or amino(lower)alkyl;
$R^5$ is hydrogen, hydroxy(lower)alkyl, protected amino(lower)alkyl, amino(lower)alkyl, carboxy(lower)alkyl or esterified carboxy(lower)alkyl;
$R^6$ is carboxy, esterified carboxy or sulfo(lower)alkyl;
$A^1$, $A^2$ and $A^3$ are each bond or lower alkylene; and
m and n are each an integer of 0 or 1;
or its pharmaceutically acceptable salt.

2. The compound of claim 1, wherein
$R^1$ is alkanoyloxy or alkenoyloxy,
$R^2$ is alkyl or alkenyl,
$R^3$ and $R^4$ are each hydroxy(lower)alkyl,
$R^5$ is carboxy(lower)alkyl or esterified carboxy(lower)alkyl,
$R^6$ is carboxy or esterified carboxy,
$A^1$, $A^2$ and $A^3$ are each bond or lower alkylene, and
m and n are each an integer of 0 or 1.

3. The compound of claim 2, wherein
$R^1$ is alkanoyloxy or alkenoyloxy,
$R^2$ is alkyl or alkenyl,
$R^3$ is hydroxy(lower)alkyl,
$R^5$ is carboxy(lower)alkyl or esterified carboxy(lower)alkyl,
$R^6$ is carboxy or esterifed carboxy,
$A^1$ and $A^2$ are each bond or lower alkylene,
m is an integer of 1 and
n is an integer of 0.

4. The compound of claim 3, which is N-[N-(3-hexadecanoyloxyoctadecanoyl)-L-threonyl]-L-glutamic acid.

5. The compound of claim 3, which is selected from the group consisting of:
dimethyl N-[N-(3-hexadecanoyloxyoctadecanoyl)-L-threonyl]-L-glutamate and dibenzyl N-[N-(3-hexadecanoyloxyoctadecanoyl)-L-threonyl]-L-glutamate.

6. The compound of claim 1, which is selected from the group consisting of:
N-[N-[15-methyl-3-(13-methyltetradecanoyloxy)hexadecanoyl]-L-valyl]-L-glutamic acid, dibenzyl N-[N-(3-hexadecanoyloxyoctadecanoyl)-L-valyl]-L-glutamate, N-[N-(3-hexadecanoyloxyoctadecanoyl)-L-valyl]-L-glutamic acid, dimethyl N-[N-(3-hexadecanoyloxyoctadecanoyl)-L-valyl]-L-glutamate, dibenzyl N-[N-(2-hexadecanoyloxyhexadecanoyl)-L-valyl]-L-glutamate, N-[N-(2-hexadecanoyloxyhexadecanoyl)-L-valyl]-L-glutamic acid, N-[N-[3-(9-octadecenoyloxy)-11-eicosenoyl]-L-valyl]-L-glutamic acid, dibenzyl N-[N-[N-(3-hexadecanoyloxyoctadecanoyl)-β-alanyl]-L-threonyl]-L-glutamate, N-[N-[N-(3-hexadecanoyloxyoctadecanoyl)-β-alanyl]-L-threonyl]-L-glutamic acid, dibenzyl N-[N-(3-hexadecanoyloxyoctadecanoyl)-β-alanyl]-L-glutamate, N-[N-(3-hexadecanoyloxyoctadecanoyl]-β- alanyl]-L-glutamic acid, dibenzyl N-[N-(3-hexadecanoyloxyoctadecanoyl)-5-aminopentanoyl]-L-glutamate, N-[N-(3-hexadecanoyloxyoctadecanoyl)-5-aminopentanoyl]-L-glutamic acid, $N^\alpha$-(3-hexadecanoyloxyoctadecanoyl)-$O^\gamma$-dibenzyl-L-glutamic acid, $N^\alpha$-[N-(3-hexadecanoyloxyoctadecanoyl)-L-phenylalanyl]-$O^\gamma$-benzyl-L-glutamic acid, N-[N-(3-hexadecanoyloxyoctadecanoyl)-L-phenylalanyl]-L-glutamic acid, N-[N-(3-hexadecanoyloxyoctadecanoyl)-β-alanyl]-L-aspartic acid, $N^\alpha$-[$N^\alpha$-(3-hexadecanoyloxyoctadecanoyl)-$O^\gamma$-benzyl-L-glutamyl]-$O^\gamma$-benzyl-L-glutamic acid, N-[N-(3-hexadecanoyloxyoctadecanoyl)-L-glutamyl]-L-glutamic acid, N-[$N^\alpha$-(3-hexadecanoyloxyoctadecanoyl)-$N^\epsilon$-benzyloxycarbonyl-L-lysyl]-L-glutamic acid, N-[N-(3-hexadecanoyloxyoctadecanoyl)-L-lysyl]-L-glutamic acid, $N^\alpha$-[N-(3-hexadecanoyloxyoctadecanoyl)-L-valyl]-$N^\epsilon$-benzyloxycarbonyl-L-lysine, N-[N-(3-hexadecanoyloxyoctadecanoyl)-L-valyl]-L-lysine, $N^\alpha$-(3-hexadecanoyloxyoctadecanoyl)-$N^\epsilon$-benzyloxycarbonyl-L-lysine, $N^\alpha$-[$N^\alpha$-(3-hexadecanoyloxyoctadecanoyl)-$N^\epsilon$-benzyloxycarbonyl-L-lysyl]-$N^\epsilon$-benzyloxycarbonyl-L-lysine, N-[N-(3-hexadecanoyloxyoctadecanoyl)-L-lysyl]-L-lysine, N-[N-(3-hexadecanoyloxyoctadecanoyl)-L-valyl]taurine, N-[N-(3-hexadecanoyloxyoctadecanoyl)glycyl]taurine, N-[N-(3-hexadecanoyloxyoctadecanoyl)-L-glutamyl]-L-threonine, N-[$N^\alpha$-(3-hexadecanoyloxyoctadecanoyl)-$N^\epsilon$-benzyloxycarbonyl-L-lysyl]-L-threonine, N-[N-(3-hexadecanoyloxyoctadecanoyl)-L-lysyl]-L-threonine and N-[N-(3-hexadecanoyloxyoctadecanoyl)-L-threonyl]-L-threonine.

7. A pharmaceutical composition comprising
(a) an anti-thrombotic effective amount of the compound of claim 1 or a pharmaceutically acceptable salt thereof; and
(b) a pharmaceutically acceptable carrier or excipient.

8. A method of treating an immune-complex disease comprising administering to a mammal in need of said treatment an amount of the compound of claim 1, effective for the treatment of said disease.

9. A method of treating an autoimmune disease comprising administering to a mammal in need of said treatment an amount of the compound of claim 1 effective for the treatment of said disease.

10. A method of treating thrombosis comprising administering to a mammal in need of said treatment an anti-thrombotic effective amount of the compound of claim 1.

11. The compound of claim 1 wherein m and n are 0 or 1, with the proviso that at least one of them is 1.

12. The compound of claim 2 wherein m and n are 0 or 1, with the proviso that at least one of them is 1.

* * * * *